United States Patent
Fabani et al.

(10) Patent No.: US 9,982,294 B2
(45) Date of Patent: May 29, 2018

(54) SEQUENCING BY ORTHOGONAL SYNTHESIS

(71) Applicant: Illumina, Inc., San Diego, CA (US)

(72) Inventors: Martin Maria Fabani, San Diego, CA (US); Maria Candelaria Rogert Bacigalupo, San Diego, CA (US); John A. Moon, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days. days.

(21) Appl. No.: 15/436,115

(22) Filed: Feb. 17, 2017

(65) Prior Publication Data

US 2017/0159118 A1 Jun. 8, 2017

Related U.S. Application Data

(63) Continuation of application No. 14/926,368, filed on Oct. 29, 2015, now Pat. No. 9,574,235, which is a continuation of application No. 14/314,864, filed on Jun. 25, 2014, now Pat. No. 9,193,999.

(60) Provisional application No. 61/842,501, filed on Jul. 3, 2013.

(51) Int. Cl.
*C12Q 1/68* (2018.01)

(52) U.S. Cl.
CPC .................................. *C12Q 1/6869* (2013.01)

(58) Field of Classification Search
None
See application file for complete search history.

(56) References Cited

U.S. PATENT DOCUMENTS

| 9,193,999 B2* | 11/2015 | Fabani | C07H 21/04 |
| 9,574,235 B2* | 2/2017 | Fabani | C12Q 1/6874 |
| 2011/0111401 A1* | 5/2011 | Korlach | C12Q 1/6869 435/6.12 |
| 2012/0115736 A1* | 5/2012 | Bjornson | C12Q 1/6869 506/2 |

* cited by examiner

*Primary Examiner* — David C Thomas
(74) *Attorney, Agent, or Firm* — Illumina, Inc.

(57) ABSTRACT

A method for sequencing includes steps of (a) providing first and second nucleic acid templates, wherein the two templates have different sequences; (b) extending a first primer bound to the first template using a first polymerase species and a first set of nucleotide analogs; (c) extending a second primer bound to the second template using a second polymerase species and a second set of nucleotide analogs, wherein the first polymerase species is different from the second polymerase species and wherein the first set of nucleotide analog is different from the second set of nucleotide analog, (d) detecting the first and second primer extension products; and (e) repeating steps (b) through (d), thereby determining the different sequences of the first and second templates.

24 Claims, 5 Drawing Sheets

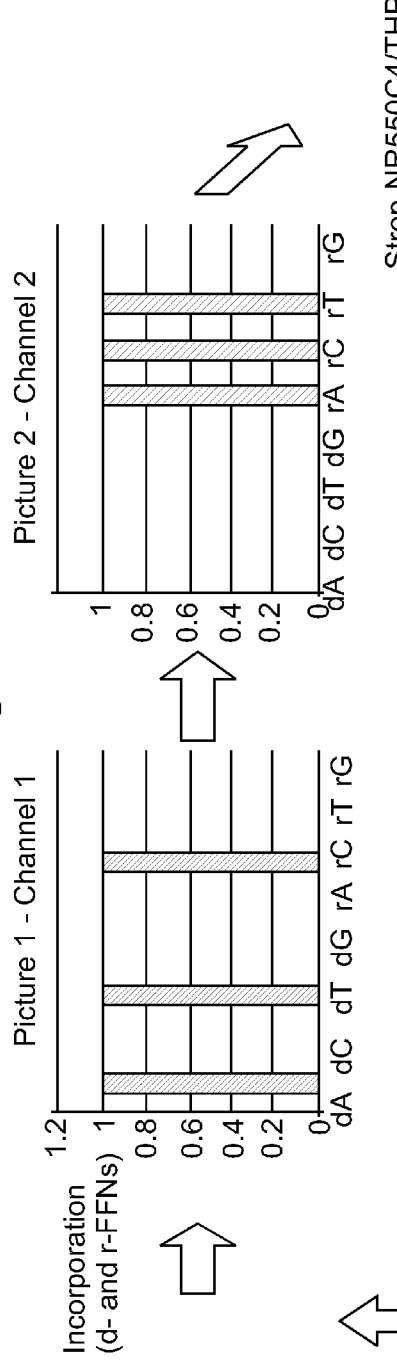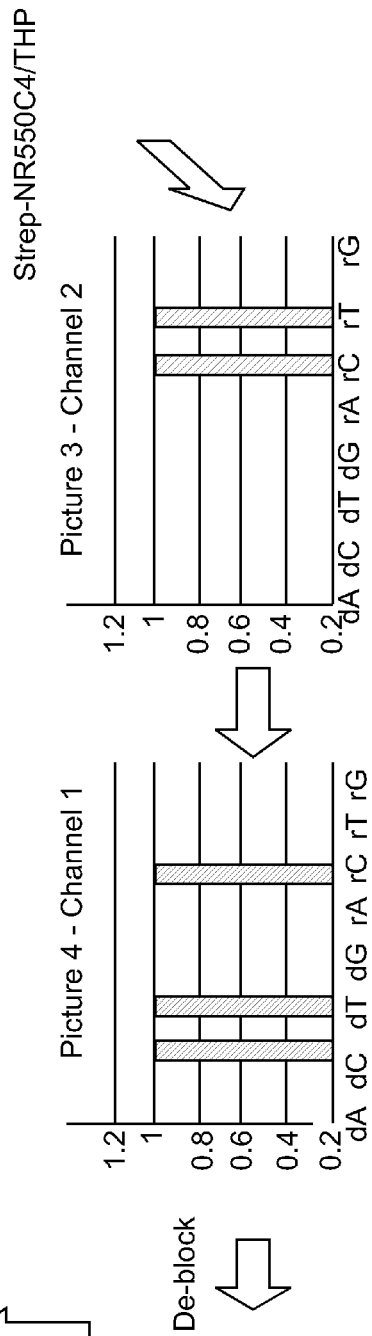
Fig. 2A
Fig. 2B

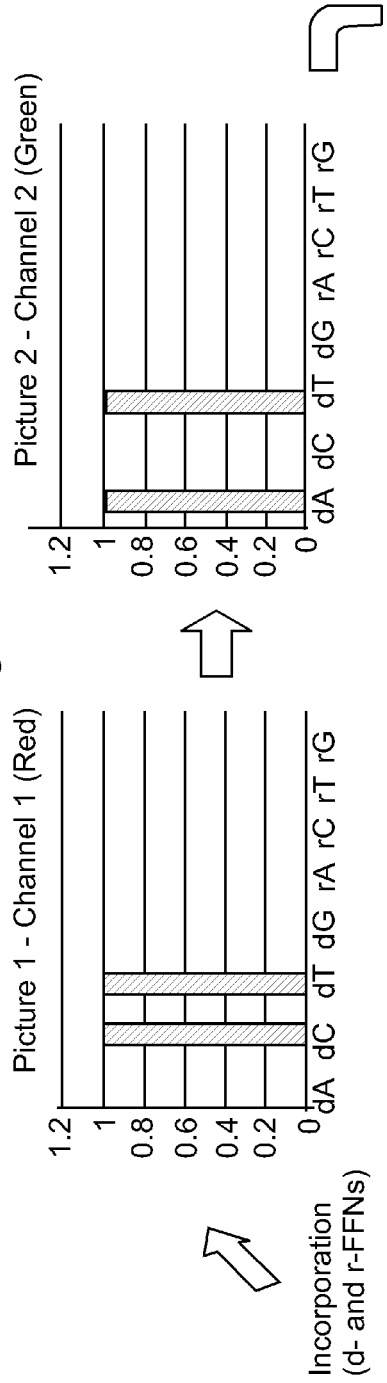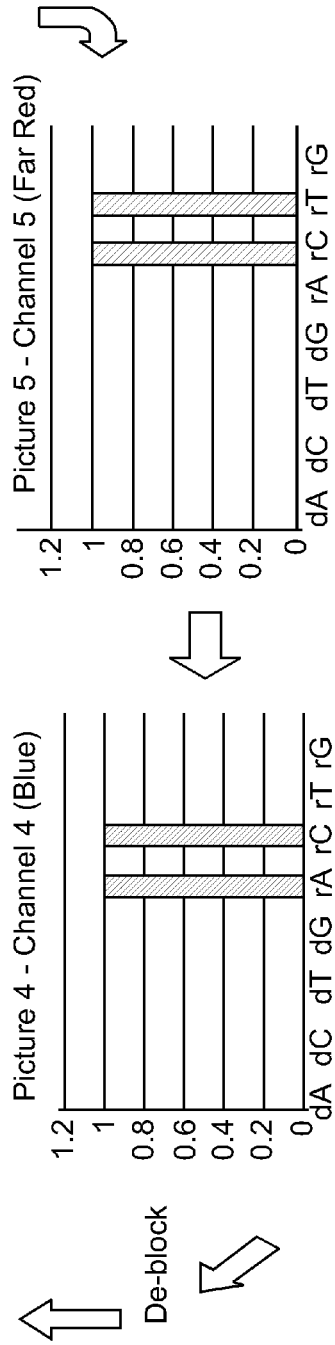
Fig. 3A
Fig. 3B

SEQUENCING BY ORTHOGONAL SYNTHESIS

CROSS-REFERENCE TO RELATED APPLICATIONS

The present application is a continuation of U.S. Nonprovisional patent application Ser. No. 14/926,368 filed on Oct. 29, 2015, which is a continuation of U.S. Nonprovisional patent application Ser. No. 14/314,864 filed on Jun. 25, 2014, now U.S. Pat. No. 9,193,999, issued Nov. 24, 2015, which claims the benefit of priority to U.S. Provisional Patent Application No. 61/842,501 filed on Jul. 3, 2013, which is hereby incorporated by reference in its entirety.

BACKGROUND

This disclosure relates generally to nucleic acid analysis, and more specifically to nucleic acid sequencing.

Currently available commercial platforms for sequencing DNA are relatively costly. These platforms use a 'sequencing-by-synthesis' approach, so called because DNA polymers are synthesized while detecting the addition of each monomer (i.e. nucleotide) to the growing polymer structure. Because a template DNA strand strictly directs synthesis of a new DNA polymer, one can infer the sequence of the template DNA from the series of nucleotide monomers that were added to the growing strand during the synthesis. The ability to detect monomer additions is facilitated by specially engineered variants of the biochemical components that normally carry out DNA synthesis in biological systems. These engineered components are relatively expensive to make and are consumed in relatively large amounts during sequencing-by-synthesis. Furthermore, monitoring the reaction uses relatively expensive hardware such as lasers, detection optics and complex fluid delivery systems. The most successful commercial platforms to date also require expensive reagents and hardware to amplify the DNA templates before sequencing-by-synthesis can even begin. The complexity and expense of these platforms has hindered their use in some clinical and research contexts where there is a clear need for the technology.

Thus, there exists a need for improvements to sequencing-by-synthesis platforms to make them more cost effective, rapid and convenient. The present disclosure addresses this need and provides other advantages as well.

BRIEF SUMMARY

The present disclosure provides a method for sequencing nucleic acid templates. The method can include steps of (a) providing an array of sites, wherein each site includes a first nucleic acid template and a second nucleic acid template, wherein the first nucleic acid template has a sequence that is different from the sequence of the second nucleic acid template; (b) extending a first primer bound to the first template using a first polymerase species and a first set of nucleotide analogs, thereby producing a first primer extension product having a first nucleotide analog at each of the sites; (c) extending a second primer bound to the second template using a second polymerase species and a second set of nucleotide analogs, thereby producing a second primer extension product having a second nucleotide analog at each of the sites, wherein the first polymerase species is different from the second polymerase species and wherein the first set of nucleotide analogs is different from the second set of nucleotide analogs; (d) detecting the first primer extension product and the second primer extension product at each of the sites; and (e) repeating steps (b) through (d), thereby determining the different sequences of the first template and the second template at each of the sites.

Also provided herein is method for sequencing nucleic acid templates that includes the steps of (a) providing a first nucleic acid template and a second nucleic acid template, wherein the first nucleic acid template has a sequence that is different from the sequence of the second nucleic acid template; (b) extending a first primer bound to the first template using a first polymerase species and a first set of nucleotide analogs, thereby producing a first primer extension product having a first nucleotide analog; (c) extending a second primer bound to the second template using a second polymerase species and a second set of nucleotide analogs, thereby producing a second primer extension product having a second nucleotide analog, wherein the first polymerase species is different from the second polymerase species and wherein the first set of nucleotide analog is different from the second set of nucleotide analog, (d) detecting the first primer extension product and the second primer extension product using a detector having a resolution that is lower than the spatial separation between the first primer extension product and the second primer extension product; and (e) repeating steps (b) through (d), thereby determining the different sequences of the first template and the second template.

BRIEF DESCRIPTION OF THE DRAWINGS

FIG. 2A shows exemplary sets of reversible terminator deoxyribonucleotides (d-FFN) and reversible terminator ribonucleotides (r-FFN) useful for a 1-dye sequencing-by-orthogonal-synthesis reaction.

FIG. 2B shows a diagrammatic representation of a reaction cycle used for a 1-dye sequencing-by-orthogonal-synthesis reaction including simulated data for signals detected in 2 different emission channels.

FIG. 3A shows exemplary sets of reversible terminator deoxyribonucleotides (d-FFN) and reversible terminator ribonucleotides (r-FFN) useful for a 2-dye sequencing-by-orthogonal-synthesis reaction.

FIG. 3B shows a diagrammatic representation of a reaction cycle used for a 2-dye sequencing-by-orthogonal-synthesis reaction including simulated data for signals detected in 4 different emission channels.

DETAILED DESCRIPTION

Figure 1A:
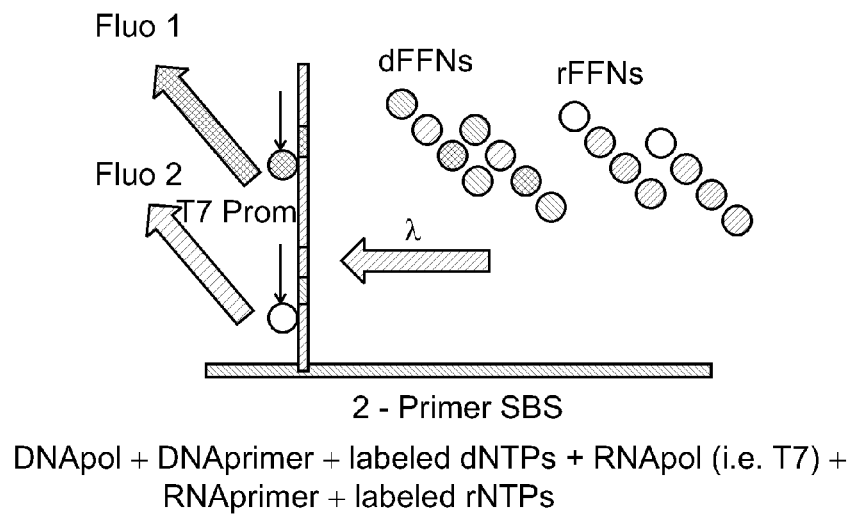
FIG. 1 shows a diagrammatic representation of a sequencing-by-orthogonal-synthesis reaction including a detection step (FIG. 1A) and a polymerase extension step (FIG. 1B).

This disclosure provides a method for high density detection of nucleic acids. Particular embodiments of the methods of the present disclosure exploit known techniques for manipulating and detecting nucleic acids. However, improvements set forth below provide orthogonal processing such that the density of information obtained from use of these techniques is increased.

The example of primer extension-based detection technique is illustrative of the increased density of information that can be obtained. Specifically, a target sequence of a nucleic acid can be hybridized to a primer and the primer extended by a DNA polymerase to add a labeled nucleotide. An array format can be used with multiple sites, each site having a single target sequence that differs from the target sequences present at other sites. Optionally several different nucleotide species, each having a distinguishable label, are used as well. Primer extension results in recruitment of the labeled nucleotide to the nucleic acid having the target sequence. In an array format, where different labeled nucleotides are used, one can distinguish the label that is recruited to each site, and use this information to identify the target nucleic acid at that site. The density of information obtained from this array format is one target sequence identified per site.

In an orthogonal format of the present disclosure, each site of the array can contain two or more different target sequences that are simultaneously detectable and distinguishable from each other. In this case the information derived from the array can be at least doubled. For example, two different primers can hybridize to the two different target sequences at each individual site. The first primer can be a DNA primer that is capable of being extended by addition of a labeled deoxyribonucleotide using a DNA polymerase and the second primer can be an RNA primer that is capable of being extended by addition of a labeled ribonucleotide using a DNA polymerase. The reagents used to extend the DNA primer are orthogonal to the reagents used to extend the RNA primer in the sense that the DNA primer extension reagents don't cross-react with the RNA primer and the RNA primer extension reagents do not cross-react with the DNA primer. The deoxyribonucleotides can have labels that are distinguishable from the labels on the ribonucleotides. The resulting orthogonality in biochemical reactivity and label management allows the DNA primer extension event to be distinguished from the RNA primer extension event at each site. Thus, the two target sequences can be distinguishably detected.

Orthogonality can result from any of a variety of biochemical components or reaction conditions that confer selectivity on two different detection events. As exemplified by reactions that use DNA polymerase and RNA polymerase, orthogonality can be derived from the specificity of two different polymerases for different primer species and for different classes of nucleotides. In some embodiments, orthogonality may instead be derived from the selectivity of different polymerases for a particular species of template (e.g. DNA vs. RNA) whether or not the polymerases are selective for a particular species of primer or class of nucleotides. Thus, it may be possible to use different polymerases that extend DNA primers with deoxyribonucleotides, but that are differentially selective for a DNA template and an RNA template, respectively. For example, DNA polymerases are generally selective for DNA templates and reverse transcriptases are generally selective for RNA templates; however, both of these enzymes can use a DNA primer and deoxyribonucleotides. Combinations of native and/or engineered polymerases are contemplated for use in orthogonal reaction systems.

The concepts of orthogonality exemplified above for a primer extension-based detection technique can be readily applied to a sequencing-by-synthesis (SBS) technique. As diagrammed in FIGS. 1A and 1B, and as set forth in further detail below, each SBS cycle can be carried out using orthogonal primers, polymerases and nucleotides to provide increased information acquisition from a flow cell or other substrate used in the SBS technique. For purposes of illustration, orthogonality will be exemplified for a sequencing approach, called "sequencing-by-orthogonal-synthesis" (SBOS); however, other methods can also benefit from orthogonal manipulation and detection as set forth in further detail below. However, the compositions, apparatus and methods set forth herein need not be limited to sequencing applications.

Orthogonality can be exploited to increase the density of information acquisition by 2-fold or more. For example, greater than 2-fold increase in information density can be obtained by using greater than two orthogonal reagent sets. As an example, 3 reagent sets can be used including (1) DNA polymerase-based extension reagents, (2) RNA polymerase-based extension reagents and (3) an engineered polymerase coupled with HNAs (1,5 anhydrohexitol nucleic acids).

As demonstrated above and as will be set forth in further detail below, the present disclosure provides the advantage of super-resolution imaging of an array, whereby the number of simultaneously resolvable target sequences at a given site is greater than one. Super-resolution imaging can provide the benefit of simultaneously distinguishing a number of different target nucleic acids that is larger than the number of sites on the array. Similarly, super-resolution is provided in that two different target sequences can be distinguished on a solid phase substrate using a detector that has a resolution that is lower than the spatial resolution that would otherwise be required to distinguish the two target sequences on the substrate.

In particular embodiments, this disclosure provides reagent and hardware configurations for efficient nucleic acid detection. An exemplary configuration uses fewer labels than the number of nucleotide species that is to be distinguished in a primer extension step. For example, four species of deoxyribonucleotide can be distinguished based on detection of a single label species. As set forth in further detail below, this can be achieved by using a first set of nucleotides including the following four species: (1) a species having a first label, (2) a species having a ligand, (3) a species having a cleavable linkage to the first label, and (4) a species lacking any label or ligand used in a subsequent step. An orthogonal set of nucleotides (e.g. ribonucleotides being orthogonal to deoxyribonucleotides) can include the following four species (5) a species having a second label, (6) a species having a mixture of the first and second labels, (7) a species having a cleavable linkage to the second label, and (8) a species lacking any label or ligand used in a subsequent step. The species within each set can be distinguished from each other based on a proper accounting of what labels appear or disappear after specific fluidic steps and the two orthogonal sets of nucleotides can be distinguished based on the two different labels. Returning to the example of the 8 species above, species (1) and (5) can be distinguished from each other based on different labels and from all other species due to their appearance after an initial labeling step and their resistance to cleaving agent; species (2) can be distinguished based on appearance of label after incubation with a labeled receptor; species (3) and (7) can be distinguished from each other based on the different labels and are distinguished from all other species based upon initial appearance of the label and then disappearance after treatment with a cleavage reagent; species (6) can be distinguished from all other species based on the presence of both labels at an intensity that is half the intensity for fully labeled species; and species (4) and (8) can be distinguished based on inference from a lack of any other species in the respective sets having been detected. Many other configurations are possible to alter the number of labels, number of fluidic manipulations during a detection phase and/or the complexity of the detection device to distinguish a certain number of labels. As such, the configuration can be tailored to suit a particular approach or application.

Terms used herein will be understood to take on their ordinary meaning unless specified otherwise. Examples of several terms used herein and their definitions are set forth below.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "cluster," when used in reference to nucleic acids, refers to a population of the nucleic acids that is attached to a solid-phase to form a feature or site. The nucleic acids are generally of a single species, thereby forming a homogenous cluster. However, in some embodiments the nucleic acids can be heterogeneous, such that individual molecules having different sequences are present at the site or feature. The nucleic acids are generally covalently attached, for example, via their 5' ends, but in some cases other attachment means are possible. The nucleic acids in a cluster can be single stranded or double stranded. In some but not all embodiments, clusters are made by a solid-phase amplification method known as bridge amplification. Exemplary configurations for clusters and methods for their production are set forth, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference.

As used herein, the term "different", when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different from each other while also having a universal sequence region that are the same as each other. Generally, when two species are referred to herein as being "different," one of the species will have a structural property that is not the same as the structural properties of the second species. For example, two different polymeric species (such as two proteins) can have different sequences of monomeric subunits (such as different sequences of amino acids for two different proteins).

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "site" means a location in an array where a particular species of molecule is present. A site can contain only a single molecule or it can contain a population of several molecules of the same species. Sites of an array are typically discrete. The discrete sites can be contiguous or they can have spaces between each other.

As used herein, the term "nucleic acid" is intended to be consistent with its use in the art and includes naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain any of a variety of analogs of these sugar moieties that are known in the art. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid are known in the art. The term "target," when used in reference to a nucleic acid, is intended as a semantic identifier for the nucleic acid in the context of a method or composition set forth herein and does not necessarily limit the structure or function of the nucleic acid beyond what is otherwise explicitly indicated.

As used herein, the term "nucleic acid template" refers to a nucleic acid or portion thereof that is capable of use as a guide for polymerase catalyzed replication. A nucleic acid molecule can include multiple templates along its length or, alternatively, only a single template may be used in a particular embodiment herein. A nucleic acid template can also function as a guide for ligase-catalyzed primer extension.

As used herein, the term "nucleotide" or "nucleotide analog" is intended to include natural nucleotides, non-natural nucleotides, ribonucleotides, deoxyribonucleotides, dideoxyribonucleotides and other molecules known as nucleotides. For example, the terms are used herein to generally refer to a nucleoside moiety (whether ribose, deoxyribose, or analog thereof) including a base moiety and optionally attached to one or more phosphate moieties. The term can be used to refer to a monomer unit that is present in a polymer, for example, to identify a subunit present in a DNA or RNA strand. The term can also be used to refer to a monomeric molecule that is not necessarily present in a polymer, for example, a molecule that is capable of being incorporated into a polynucleotide in a template dependent manner by a polymerase.

Exemplary nucleotides include, but are not limited to, ribonucleotide monophosphate (sometimes referred to as a ribonucleoside monophosphate), ribonucleotide diphosphate (sometimes referred to as a ribonucleoside diphosphate), ribonucleotide triphosphate (sometimes referred to as a ribonucleoside triphosphate), deoxynucleotide monophosphate (sometimes referred to as a deoxynucleoside monophosphate), deoxynucleotide diphosphate (sometimes referred to as a deoxynucleoside diphosphate) and deoxynucleotide triphosphate (sometimes referred to as a deoxynucleoside triphosphate). For clarity when wishing to distinguish RNA components from DNA components, the term "ribonucleotide" can be used to specify RNA nucleotides, such as ribouridine triphosphate, riboguanidine triphosphate, ribocytidine triphosphate or riboadenosine triphosphate; and the term "deoxynucleotide" can be used to specify DNA nucleotides, such as deoxythymidine triphosphate, deoxyguanidine triphosphate, deoxycytidine triphosphate and deoxyadenosine triphosphate. In particular embodiments, the nucleotides are 'extendable', for example, lacking an extension blocking moiety at the 3' hydroxyl or at any other position on the nucleotide. In other embodiments, the nucleotides are 'blocked,' having a moiety that prevents the 3' position from participating in extension by addition of another nucleotide or oligonucleotide.

As used herein, the term "primer" means a nucleic acid having a sequence that binds to a primer binding site at or near a template sequence. Generally, the primer binds in a configuration that allows replication of the template, for example, via polymerase extension of the primer. The primer can be a first portion of a nucleic acid molecule that binds to a second portion of the nucleic acid molecule, the first portion being a primer sequence and the second portion being a primer binding sequence (e.g. a hairpin primer). Alternatively, the primer can be a first nucleic acid molecule that binds to a second nucleic acid molecule having the template sequence. A primer can consist of DNA, RNA or analogs thereof.

As used herein, the term "primer extension product" means a primer that has been modified by addition of at least one nucleotide analog. For example, a primer can be modified by addition of one or more nucleotide analogs to its 3' end (e.g. via polymerase catalysis), thereby forming a primer extension product. A primer extension product can alternatively be produced by ligation of an oligonucleotide to the 3' or 5' end of a primer. In this case, the primer extension product is extended by a length equivalent to the length of the oligonucleotide. A primer extension product can be at least 1, 2, 5, 10, 500, 1000 or more nucleotides longer than the primer. Alternatively or additionally, a primer extension product can be no more than 1, 2, 5, 10, 500, or 1000 nucleotides longer than the primer. For example, use of a blocked nucleotide provides for an extension product that is at least 1 nucleotide longer than the primer and also no more than 1 nucleotide longer than the primer.

As used herein, reference to "selectively" manipulating (or "selective" manipulation of) a first thing compared to second thing is intended to mean that the manipulation has a greater effect on the first thing compared to the effect on the second thing. The manipulation need not have any effect on the second thing. The manipulation can have an effect on the first thing that is at least 1%, 5%, 10%, 25%, 50%, 75%, 90%, 95%, or 99% greater than the effect on the second thing. The manipulation can have an effect on the first thing that is at least 2 fold, 3 fold, 4 fold, 5 fold, 10 fold, 100 fold, 1×103 fold, 1×104 fold or 1×106 fold higher than the effect on the second thing. The manipulation can include, for example, modifying, contacting, treating, changing, cleaving (e.g. of a chemical bond), photo-chemically cleaving (e.g. of a chemical bond), forming (e.g. of a chemical bond), photo-chemically forming (e.g. of a chemical bond), covalently modifying, non-covalently modifying, destroying, photo-ablating, removing, synthesizing, polymerizing, photo-polymerizing, amplifying (e.g. of a nucleic acid), copying (e.g. of a nucleic acid), extending (e.g. of a nucleic acid), ligating (e.g. of a nucleic acid), or other manipulation set forth herein or otherwise known in the art.

As used herein, the term "sequence," when used in reference to a nucleic acid, refers to the order of nucleotides (or bases) in the nucleic acids. In cases where, different species of nucleotides are present in the nucleic acid, the sequence includes an identification of the species of nucleotide (or base) at respective positions in the nucleic acid. A sequence is a property of all or part of a nucleic acid molecule. The term can be used similarly to describe the order and positional identity of monomeric units in other polymers such as amino acid monomeric units of protein polymers.

As used herein, the term "species" is used to identify molecules that share the same chemical structure. For example, a mixture of nucleotides can include several dCTP molecules. The dCTP molecules will be understood to be the same species as each other, but a different species compared to dATP, dGTP, dTTP etc. Similarly, individual DNA molecules that have the same sequence of nucleotides are the same species, whereas DNA molecules with different sequences are different species. As another example, a DNA polymerase is a different polymerase species compared to an RNA polymerase (even if the tow polymerases are derived from the same organism).

The embodiments set forth below and recited in the claims can be understood in view of the above definitions.

The present disclosure provides a method for sequencing nucleic acid templates. The method can include steps of (a) providing an array of sites, wherein each site includes a first nucleic acid template and a second nucleic acid template, wherein the first nucleic acid template has a sequence that is different from the sequence of the second nucleic acid template; (b) extending a first primer bound to the first template using a first polymerase species and a first set of nucleotide analogs, thereby producing a first primer extension product having a first nucleotide analog at each of the sites; (c) extending a second primer bound to the second template using a second polymerase species and a second set of nucleotide analogs, thereby producing a second primer extension product having a second nucleotide analog at each of the sites, wherein the first polymerase species is different from the second polymerase species and wherein the first set of nucleotide analogs is different from the second set of nucleotide analogs; (d) detecting the first primer extension product and the second primer extension product at each of the sites; and (e) repeating steps (b) through (d), thereby determining the different sequences of the first template and the second template at each of the sites.

Also provided herein is method for sequencing nucleic acid templates that includes the steps of (a) providing a first nucleic acid template and a second nucleic acid template, wherein the first nucleic acid template has a sequence that is different from the sequence of the second nucleic acid template; (b) extending a first primer bound to the first template using a first polymerase species and a first set of nucleotide analogs, thereby producing a first primer extension product having a first nucleotide analog; (c) extending a second primer bound to the second template using a second polymerase species and a second set of nucleotide analogs, thereby producing a second primer extension product having a second nucleotide analog, wherein the first polymerase species is different from the second polymerase species and wherein the first set of nucleotide analog is different from the second set of nucleotide analog, (d) detecting the first primer extension product and the second primer extension product using a detector having a resolution that is lower than the spatial separation between the first primer extension product and the second primer extension product; and (e) repeating steps (b) through (d), thereby determining the different sequences of the first template and the second template.

As set forth above, a method of the present disclosure can include a step of providing first and second nucleic acid templates, wherein the sequences for the two templates are different. The two template sequences can be portions of a single nucleic acid molecule or, alternatively, the two template sequences can be located on separate molecules. As set forth in further detail elsewhere herein, the two template sequences may be in a proximity that is too close to spatially resolve with the detection system used. Nevertheless, the orthogonal detection methods of the present disclosure allow these template sequences to be distinguished. The orthogonal detection scheme is exemplified for two template sequences, but can be used with two or more template sequences. Accordingly, a system or method set forth herein can include at least 2, 3, 4, 5, 10 or more template sequences that are in close proximity, for example on a single nucleic acid molecule, at a single site of an array, or otherwise in a proximity that is too close to spatially resolve with the detection system used.

Target nucleic acids used herein can be composed of DNA, RNA or analogs thereof. The source of the target nucleic acids can be genomic DNA, messenger RNA, or other nucleic acids from native sources. In some cases the target nucleic acids that are derived from such sources can be amplified prior to use in a method or composition herein.

Exemplary biological samples from which target nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *dictyostelium discoideum*; a fungi such as *pneumocystis carinii, Takifugu rubripes*, yeast, *Saccharamoyces cerevisiae* or *Schizosaccharomyces pombe*; or a *plasmodium falciparum*. Target nucleic acids can also be derived from a prokaryote such as a bacterium, *Escherichia coli*, staphylococci or *mycoplasma pneumoniae*; an archae; a virus such as Hepatitis C virus or human immunodeficiency virus; or a viroid. Target nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

Figure 4:
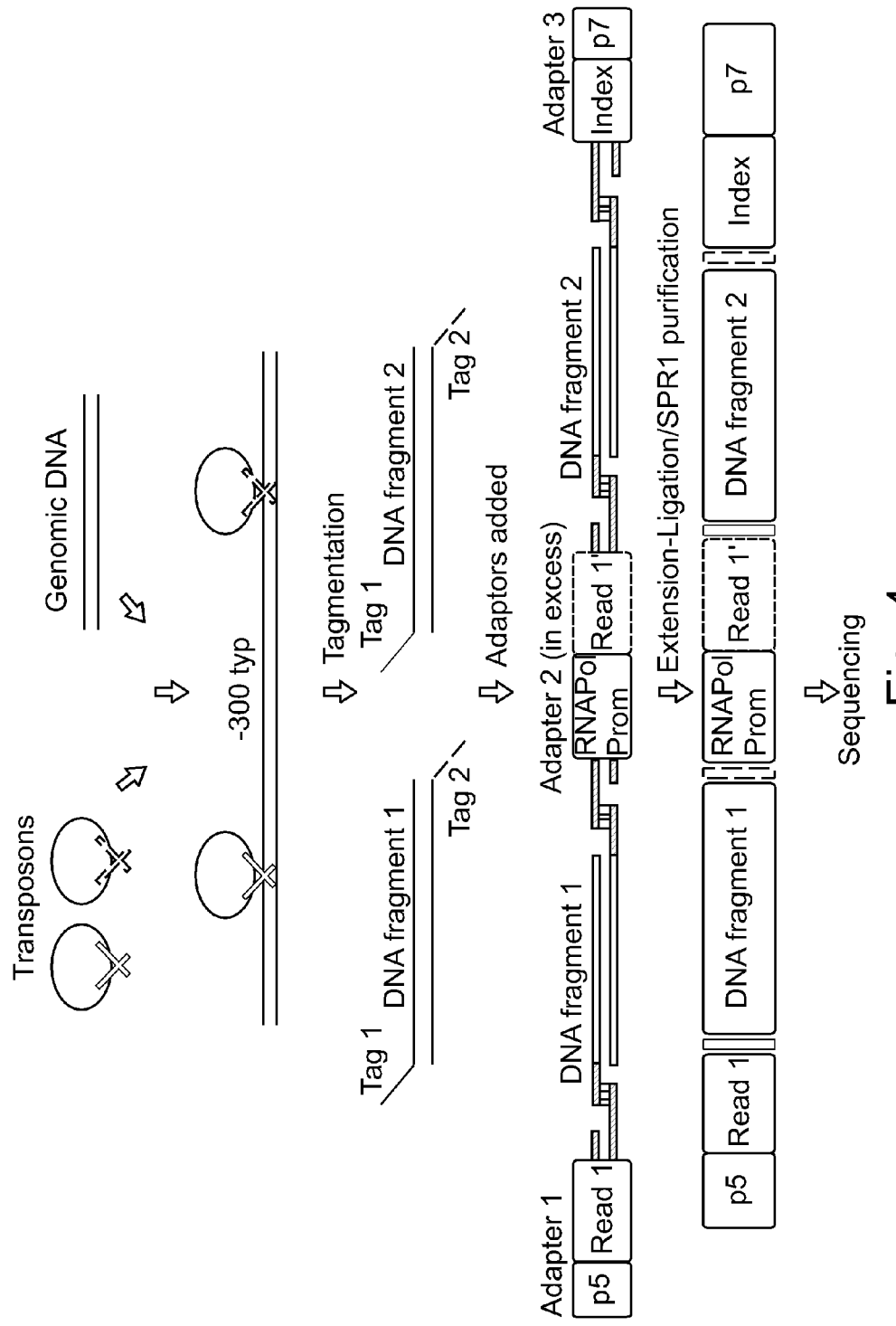
FIG. 4 shows a diagrammatic representation of a method for preparing templates for a sequencing-by-orthogonal-synthesis reaction.

In particular embodiments, a nucleic acid sample can be modified or prepared for use in one or more of the methods set forth herein. In some cases it is desired to add one or more primer binding sites to a nucleic acid. Known molecular biological techniques can be used to introduce primer binding sites upstream of respective template sequences, for example, via insertion of an adapter having the primer binding site, mutation to create the primer binding site, ligation of an adapter having the primer binding site etc. Useful methods are described in Sambrook et al., supra and Ausubel et al., supra. Example I provides an illustration of a tagmentation-based technique. Tagmentation is particularly useful for introducing one or more primer binding sites and can be carried out, for example, using techniques set forth in U.S. Pat. Nos. 6,294,385 and 8,383,345, and PCT Pub. No. WO 2012/106546, each of which is incorporated herein by reference. It will be understood that in some cases naturally occurring sequence regions that reside upstream of respective template sequences can be exploited as a primer binding sites in a method set forth herein. Methods similar to those exemplified above for primer binding sites can be used to introduce other desired sequence elements such as promoter elements for RNA polymerase-based extension or tag sequences. An exemplary method for creating nucleic acid fragments each having a first template sequence in proximity to a DNA priming site and a second template sequence in proximity to an RNA priming site and RNA polymerase promoter is shown in FIG. 4 and described in Example I.

Universal priming sites are particularly useful for multiplex applications of the methods set forth herein. The term "universal," when used in reference to nucleic acids, means a region of sequence that is common to two or more nucleic acid molecules where the molecules also have regions of different sequence. A universal sequence present in different members of a collection of molecules can allow the replication, amplification or detection of multiple different sequences using a single universal primer species that is complementary to the universal sequence. Thus a universal primer includes a sequence that can hybridize specifically to a universal sequence. Examples of methods of attaching universal sequences to a collection of target nucleic acids can be found in US Pat. App. Pub. No. 2007/0128624 A1, which is incorporated herein by reference.

Any of a variety of promoters can be used as appropriate for the particular RNA polymerase to be used. For example, a bacterial promoter can be used with a bacterial RNA polymerase or a eukaryotic promoter can be used with a eukaryotic RNA polymerase. A promoter will generally be located near the template that is to be detected, upstream of the RNA primer binding site and on the same strand as the template. Standard nucleic acid synthesis and/or molecular biological techniques can be used to create a functional promoter construct in a target nucleic acid. A particularly useful promoter is a bidirectional promoter such as those present in mammalian bi-directional gene pairs. A bi-directional promoter can be useful for paired end sequencing applications such as those set forth in further detail below.

In some embodiments, target nucleic acids can be obtained as fragments of one or more larger nucleic acids. Fragmentation can be carried out using any of a variety of techniques known in the art including, for example, nebulization, sonication, chemical cleavage, enzymatic cleavage, or physical shearing. Fragmentation may also result from use of a particular amplification technique that produces amplicons by copying only a portion of a larger nucleic acid. For example, PCR amplification produces fragments having a size defined by the length of the fragment between the flanking primers used for amplification.

A population of target nucleic acids, or amplicons thereof, can have an average strand length that is desired or appropriate for a particular application of the methods or compositions set forth herein. For example, the average strand length can be less than about 100,000 nucleotides, 50,000 nucleotides, 10,000 nucleotides, 5,000 nucleotides, 1,000 nucleotides, 500 nucleotides, 100 nucleotides, or 50 nucleotides. Alternatively or additionally, the average strand length can be greater than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The average strand length for population of target nucleic acids, or amplicons thereof, can be in a range between a maximum and minimum value set forth above. It will be understood that amplicons generated at an amplification site (or otherwise made or used herein) can have an average strand length that is in a range between an upper and lower limit selected from those exemplified above.

In some cases a population of target nucleic acids can be produced or otherwise configured to have a maximum length for its members. For example, the maximum length for the members that are made or used as set forth herein can be less than about 100,000 nucleotides, 50,000 nucleotides, 10,000 nucleotides, 5,000 nucleotides, 1,000 nucleotides, 500 nucleotides, 100 nucleotides or 50 nucleotides. Alternatively or additionally, a population of target nucleic acids, or amplicons thereof, can be produced under conditions or otherwise configured to have a minimum length for its members. For example, the minimum length for the members that are used in one or more steps of a method set forth herein or that are present in a particular composition can be more than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The maximum and minimum strand length for target nucleic acids in a population can be in a range between a maximum and minimum value set forth above. It will be understood that amplicons generated at an amplification site (or otherwise made or used herein) can have maximum and/or minimum strand lengths in a range between the upper and lower limits exemplified above.

Any of a variety of known amplification techniques can be used to increase the amount of template sequences present for use in a method set forth herein. Exemplary techniques include, but are not limited to, polymerase chain reaction (PCR), rolling circle amplification (RCA), multiple displacement amplification (MDA), or random prime amplification (RPA) of nucleic acid molecules having template sequences. It will be understood that amplification of target nucleic acids prior to use in a method or composition set forth herein is optional. As such, target nucleic acids will not be amplified prior to use in some embodiments of the methods and compositions set forth herein. Target nucleic acids can optionally be derived from synthetic libraries. Synthetic nucleic acids can have native DNA or RNA compositions or can be analogs thereof. Solid-phase amplification methods can also be used, including for example, cluster amplification, bridge amplification or other methods set forth below in the context of array-based methods.

A nucleic acid used in a method set forth herein can be solution phase or solid-phase. The nucleic acid when in solution phase is generally soluble, but can also be in a suspended form that is capable of being precipitated, as is the case for some large nucleic acid species such as chromosomes or nucleic acid nanoballs (see, for example, US Pat. Publ. No. 2007/0099208 A1, which is incorporated herein by reference). A nucleic acid that is solid-phase can occur in or on a solid-phase support. Exemplary solid-phase supports include those made from glass, nitrocellulose, silica, metal, plastic and other materials set forth elsewhere herein, for example, with regard to array formats and flow cells. Similarly, a nucleic acid can occur in or on a semisolid support such as a gel. Exemplary gels that are useful include, but are not limited to, those having a colloidal structure, such as agarose; polymer mesh structure, such as gelatin; or cross-linked polymer structure, such as polyacrylamide. Hydrogels are particularly useful such as those set forth in US Pat. Pub. No. 2011/0059865 A1 and U.S. patent application Ser. No. 13/784,368, each of which is incorporated herein by reference.

Attachment of a nucleic acid to a support, whether rigid or semi-rigid, can occur via covalent or non-covalent linkage(s). Exemplary linkages are set forth in U.S. Pat. Nos. 6,737,236; 7,259,258; 7,375,234 and 7,427,678; and US Pat. Pub. No. 2011/0059865 A1, each of which is incorporated herein by reference. In some embodiments, a nucleic acid or other reaction component can be attached to a gel or other semisolid support that is in turn attached or adhered to a solid-phase support. In such embodiments, the nucleic acid or other reaction component will be understood to be solid-phase.

Orthogonal detection systems can be based on use of two or more reagent systems for primer extension, wherein the components of the two reagent systems do not substantially cross-react. For example, a first reagent system can include a DNA polymerase, deoxyribonucleotides and a DNA primer; and a second reagent system can include an RNA polymerase, ribonucleotides and an RNA primer. Both systems are capable of acting on a DNA template, for example, one having a first priming site that is complementary to the DNA primer and a second priming site that is complementary to the RNA primer. However, the DNA polymerase is specific for the DNA primer and deoxyribonucleotides such that it selectively extends the DNA primer with the deoxyribonucleotides instead of the ribonucleotides. Conversely, the RNA polymerase is specific for the RNA primer and ribonucleotides such that it selectively extends the RNA primer with the ribonucleotides instead of the deoxyribonucleotides. Similarly, orthogonality can be achieved using other specific reagent systems such as an engineered polymerase that selectively incorporates HNAs (1,5 anhydrohexitol nucleic acids) into a primer made from HNA monomers. HNA-based primer extension is orthogonal to DNA polymerase and RNA polymerase extension systems. Exemplary conditions and reagents that can be used for HNA-based primer extension are described in Pinheiro et al, Science, 336 (6079):341-344 (2012) and Cozens et al, Proc. Nat'l. Acad. Sci. USA, 109 (21):8067-8072 (2012), each of which is incorporated herein by reference.

In accordance with the exemplary embodiments set forth above, deoxyribonucleotides can be considered to be an orthogonal class of nucleotides with respect to ribonucleotides and HNAs. Similarly, in the context of particular embodiments, the classes of DNA polymerases and RNA polymerases are orthogonal to each other, and the classes of DNA primers and RNA primers are orthogonal to each other. Generally orthogonality can be exploited in a method set forth herein when a first polymerase is selective for a first class of nucleotide analogs compared to a second class of nucleotide analogs and wherein a second polymerase is selective for the second class of nucleotide analogs compared to the first class of nucleotide analogs. Similarly, orthogonality can exist when the first polymerase is selective for a first class of primer compared to a second class of primer and when the second polymerase is selective for the second class of primer compared to the first class of primer.

Any of a variety of polymerases can be used in a method or composition set forth herein including, for example, protein-based enzymes isolated from biological systems and functional variants thereof. Reference to a particular polymerase, such as those exemplified below, will be understood to include functional variants thereof unless indicated otherwise. A particularly useful function of a polymerase is to catalyze the polymerization of a nucleic acid strand using an existing nucleic acid as a template. Other functions that are useful are described elsewhere herein. Examples of useful polymerases include DNA polymerases, reverse transcriptases and RNA polymerases.

A polymerase having an intrinsic 3' to 5' proofreading exonuclease activity can be useful for some embodiments. Polymerases that substantially lack 3' to 5' proofreading exonuclease activity are also useful in some embodiments, for example, in most sequencing embodiments. Absence of exonuclease activity can be a wild type characteristic or a characteristic imparted by a variant or engineered polymerase structure. For example, exo minus Klenow fragment is a mutated version of Klenow fragment that lacks 3' to 5' proofreading exonuclease activity.

Depending on the embodiment that is to be used, a polymerase can be either thermophilic or heat inactivatable. Thermophilic polymerases are typically useful for high temperature conditions or in thermocycling conditions such as those employed for polymerase chain reaction (PCR) techniques. Examples of thermophilic polymerases include, but are not limited to 9° N DNA Polymerase, Taq DNA polymerase, Phusion® DNA polymerase, Pfu DNA polymerase, RB69 DNA polymerase, KOD DNA polymerase, and VentR® DNA polymerase. Most polymerases isolated from non-thermophilic organisms are heat inactivatable. Examples are DNA polymerases from phage. It will be understood that polymerases from any of a variety of sources can be modified to increase or decrease their tolerance to high temperature conditions. Particularly useful polymerases for incorporating nucleotides having labels and/or reversible terminating moieties are described in US 2006/0281109 A1, which is incorporated herein by reference.

Another orthogonal reagent system of primer extension is a ligase based system that is selective for incorporation of oligonucleotides instead of monomeric nucleotides that are incorporated by the polymerase-based extension systems described above. A DNA ligase reagent system is fully orthogonal with an RNA polymerase based reagent system when used under conditions wherein DNA primer is extended by the DNA ligase but not by RNA polymerase and wherein an RNA primer is extended by the RNA polymerase but not by the DNA ligase. Extension by ligation can be carried out in a sequencing application using a population of partially random probe oligonucleotides having a one- or two-base encoding scheme. Ligation based extension techniques that can be used for detection in an extension reaction such as in a sequencing context are set forth in McKernan et al., Genome Research 19 (9): 1527-41 (2009); Shendure et al., Science 309:1728-1732 (2005); and U.S. Pat. Nos. 5,599,675 and 5,750,341, each of which is incorporated herein by reference.

Orthogonal manipulation and detection in accordance with the present disclosure does not require that two template sequences differ at every position along their length. Rather, the same base moiety can be present at positions that are detected on a first template and second template, respectively. The two positions can be distinguished based on the distinguishable characteristics of the labels present in the orthogonal reagent systems and the specificity of the reagent systems for extending the appropriate primer. This information can in turn be used to distinguishably detect the two different template sequences, even if the two positions are detected simultaneously using a detector having a resolution that is too low to resolve points at distance equivalent to the spacing of the two template sequences.

Any of a variety of labels can be used. A label moiety that is particularly useful when used for detection of a nucleotide analog, can be any part of the nucleotide analog that provides a distinguishable characteristic when compared to other molecules present in its environment. The distinguishable characteristic can be, for example, an optical signal such as absorbance of radiation, fluorescence emission, luminescence emission, fluorescence lifetime, fluorescence polarization, or the like; binding affinity for a ligand or receptor; magnetic properties; electrical properties; charge; mass; radioactivity or the like. Exemplary label moieties include, without limitation, a fluorophore, luminophore, chromophore, radioactive isotope, mass label, charge label, spin label, receptor, ligand, or the like. The label moiety can be part of a nucleotide that is a monomer unit present in a nucleic acid polymer or the label moiety can be a part of a free nucleotide analog (e.g. a nucleotide triphosphate).

Fluorophores are particularly useful and include, for example, fluorescent nanocrystals; quantum dots, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue, Texas Red, Alexa dyes, SETA dyes, Atto dyes, phycoerythin, bodipy, and analogs thereof. Useful optical probes are described in Lakowicz, Principles of Fluorescence Spectroscopy, 3rd Ed. Springer (2006); Haugland, Handbook of Fluorescent Probes and Research Products 9th Ed., Molecular Probes, Inc, (2002); Shapiro, Practical Flow Cytometry, 4th Ed., John Wiley & Sons (2003); WO 98/59066; WO 91/06678 or US Pat. Appl. Publ. No. 2010/0092957 A1, each of which is incorporated herein by reference.

Other labels, some of which are non-optical labels, can be used in various embodiments of the methods and compositions set forth herein. Examples include, without limitation, an isotopic label such as a naturally non-abundant radioactive or heavy isotope; magnetic substance; electron-rich material such as a metal; electrochemiluminescent label such as Ru(bpy)32+; or moiety that can be detected based on a nuclear magnetic, paramagnetic, electrical, charge to mass, or thermal characteristic. Labels can also include magnetic particles or optically encoded nanoparticles. Such labels can be detected using appropriate methods known to those skilled in the art. For example, a charged label can be detected using an electrical detector such as those used in commercially available sequencing systems from Ion Torrent (Guilford, Conn., a Life Technologies subsidiary) or detection systems described in US Pat. App. Publ. Nos. 2009/0026082 A1; 2009/0127589 A1; 2010/0137143 A1; and 2010/0282617 A1, each of which is incorporated herein by reference. It will be understood that for some embodiments a nucleotide analog need not have one or more of the labels set forth herein.

A label moiety can be attached to a nucleotide in a variety of ways. Exemplary attachments and label compositions that are useful for nucleotides are set forth in Bentley et al., Nature 456:53-59 (2008), WO 04/018497; U.S. Pat. No. 7,057,026; WO 91/06678; WO 07/123744; U.S. Pat. No. 7,329,492; U.S. Pat. No. 7,211,414; U.S. Pat. No. 7,315,019; U.S. Pat. No. 7,405,281, and US 2008/0108082, each of which is incorporated herein by reference.

In particular embodiments, for example, those that utilize cyclic primer extension in a sequencing-by-orthogonal-synthesis approach, the nucleotides can include reversible terminator moieties. Reversible terminator moieties provide a convenient way to control an extension reaction to add only a single nucleotide to a primer until a subsequent deblocking step is carried out. This can be understood in the context of a sequencing approach as follows. To initiate a first sequencing cycle, one or more labeled nucleotides, DNA polymerase, etc., can be delivered to an array of primer-bound, nucleic acid templates. Optionally, the nucleotides can include a reversible terminator moiety such that subsequent extension cannot occur until a deblocking agent is delivered to remove the moiety. Two or more labels added to the sites by the primer extension reactions can be detected, for example, using methods or apparatus set forth herein. A deblocking reagent can be contacted with the array (before or after detection occurs) to remove the reversible terminator. Washes can be carried out between the various delivery steps. The cycle can then be repeated n times to extend the primers by n nucleotides, thereby detecting sequences of length n. Exemplary sequencing techniques and useful reagents are described, for example, in Bentley et al., Nature 456:53-59 (2008), WO 04/018497; U.S. Pat. No. 7,057,026; WO 91/06678; WO 07/123744; U.S. Pat. No. 7,329,492; U.S. Pat. No. 7,211,414; U.S. Pat. No. 7,315,019; U.S. Pat. No. 7,405,281, and US 2008/0108082, each of which is incorporated herein by reference.

An orthogonal sequencing method set forth herein can be utilized in a paired-end sequencing approach. Generally, paired end sequencing involves determining the sequences at two ends of a template sequence region, wherein the length of the template sequence region is known. Methods for fragmenting a target nucleic acid sample (e.g. genomic DNA sample), attaching primers to accommodate paired end reads and reading sequence from the ends of the fragments are known and can be carried out as described, for example, in U.S. Pat. Nos. 7,754,429; 8,017,335; and 8,192,930, each of which is incorporated herein by reference.

Figure 5:
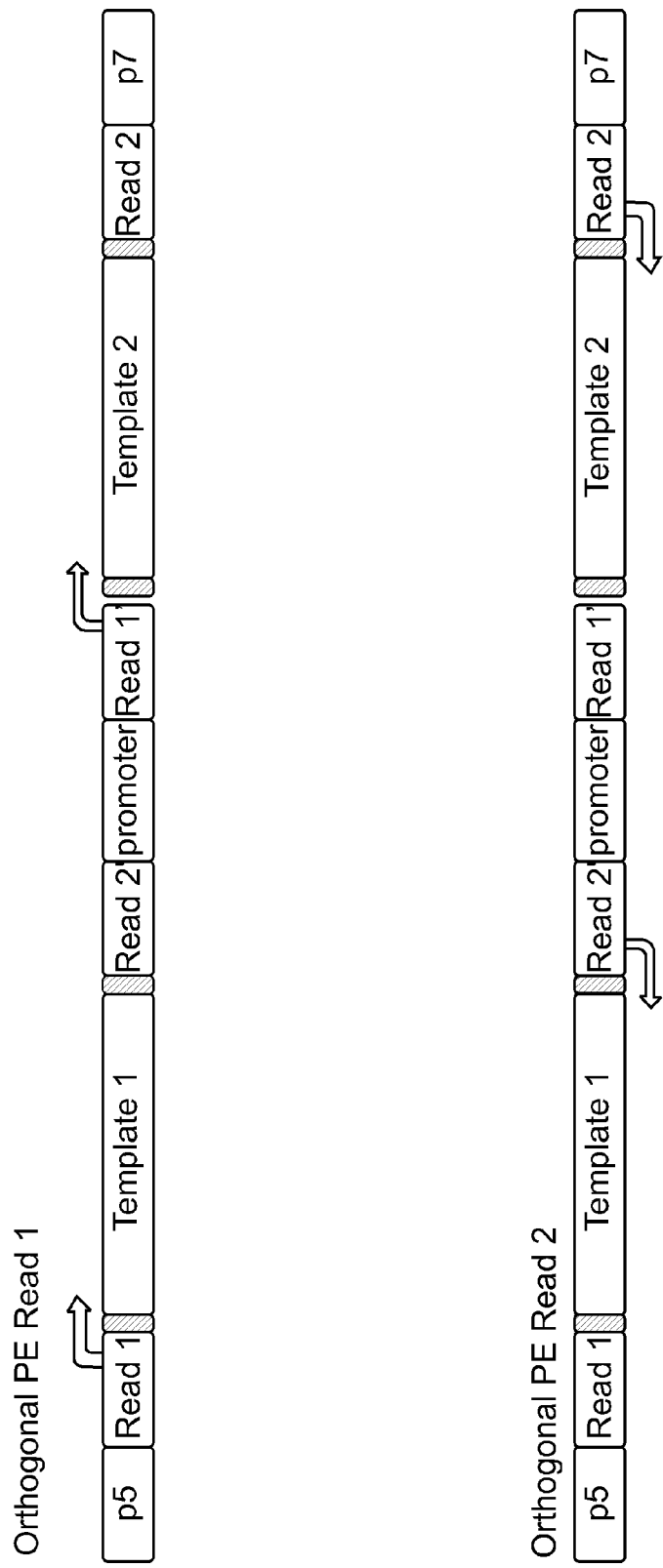
FIG. 5 shows a construct for sequencing-by-orthogonal-synthesis in a paired end format.

In the case of a sequencing-by-orthogonal-synthesis embodiment, nucleic acid fragments can be constructed to have two template sequences and paired reads can be obtained from each of the two templates to obtain 4 reads from a single fragment. Paired end reads can be facilitated by use of a bidirectional promoter flanked by RNA polymerase binding sites. An exemplary construct is shown in FIG. 5. In this example, the construct includes the Read 1 and Read 1' priming sites for a first orthogonal read. In the first orthogonal read a DNA primer can hybridize to the Read 1 priming site to allow DNA polymerase catalyzed reading of the sequence at a first end of Template 1 (indicated by the closed arrow in the upper diagram). Also in the first orthogonal read, the Read 1' priming site can hybridize to an RNA primer and due to the proximity of the bidirectional promoter RNA polymerase can read a first end of template 2 (indicated by the open arrow in the upper diagram). A second orthogonal read can be obtained by hybridizing a DNA primer to the Read 2 priming site and reading the second end of Template 2 and hybridizing an RNA primer to the Read 2' priming site and reading the second end of Template 1 (indicated by the closed arrow in the lower diagram). The proximity of the bidirectional promoter to the Read 2' priming site allows the RNA polymerase extension to occur (indicated by the open arrow in the lower diagram). The construct exemplified in FIG. 5 can be made, for example, using the methods described in FIG. 4.

A bidirectional promoter is not necessary for paired end reads using an RNA polymerase in a sequencing-by-orthogonal-synthesis embodiment. Rather, RNA priming sites and their promoters can be located at the ends of a 2-template construct and the adapter that links the two templates can contain DNA priming sites. Taking the construct of FIG. 5 as an example, the positions of the Read 1 and Read 1' priming sites can be swapped, the positions of the Read 2 and Read 2' priming sites can be swapped, the bidirectional promoter can be removed and separate RNA promoters can be located upstream of the Read 1' and Read 2' priming sites, respectively.

A nucleic acid extension reaction, or other cyclic reaction, that is carried out using methods set forth herein can proceed for one or more cycles. In particular embodiments, a multicycle reaction can include at least 2 cycles, 5 cycles, 10 cycles, 50 cycles, 100 cycles, 500 cycles, 1,000 cycles, 5,000 cycles, 10,000 cycles or more. Alternatively or additionally, a reaction can have an upper limit whereby no more than 1 cycle, 2 cycles, 5 cycles, 10 cycles, 50 cycles, 100 cycles, 500 cycles, 1,000 cycles, 5,000 cycles, or 10,000 cycles occur. In some embodiments, each cycle will result in the incorporation of a single nucleotide analog into an extended primer. In this case, the minimum or maximum number of cycles exemplified above can be understood to exemplify the minimum or maximum number of nucleotides incorporated into an extension product in a polymerase catalyzed reaction.

Some embodiments can use non-cyclic extension reactions such as single base extension (SBE) or allele specific primer extension (ASPE) reactions. Reversible terminator moieties can be used for non-cyclic extension. Since a deblocking step is not necessary for these non-cyclic reactions, the nucleotides can instead be non-reversibly terminated. For example, dideoxynucleotides can be used. Exemplary reagents and related techniques for SBE, ASPE and other useful non-cyclic extension techniques are described, for example, in U.S. Pat. No. 7,670,810 and U.S. Pat. App. Pub. Nos. 2003/0108867; 2003/0108900; 2003/0170684; 2003/0207295; or 2005/0181394, each of which is incorporated herein by reference. An example of a commercially available product that uses a non-cyclic extension technique and that can be modified to increase information content via the orthogonal detection methods set forth herein is the Infinium® genotyping product available from Illumina, Inc. (San Diego, Calif.).

Cyclic and non-cyclic reactions alike can include steps where reaction components are separated from each other or removed from the reaction environment. One or more reaction components can be separated, for example, by separation of solid-phase components from liquid-phase components. Wash steps can optionally be included in order to more completely remove unwanted liquid-phase component(s) from solid-phase component(s). A particularly useful reaction vessel for such separations is a flow cell such as those commonly used in cyclical sequencing procedures. Exemplary flow cells, methods for their manufacture and methods for their use are described in US Pat. App. Publ. Nos. 2010/0111768 A1 and 2012/0270305 A1; and WO 05/065814, each of which is incorporated herein by reference. Whether or not solid-phase separation methods are used, reaction components can be removed by any of a variety of other techniques known in the art including, liquid-liquid extraction, solid-phase extraction, chromatography, filtration, centrifugation or the like Detection can be carried out in a method of the present disclosure using an apparatus suited to the particular label in use. For example, an optical detector such as a fluorescence detector, absorbance detector, luminescence detector or the like can be used to detect appropriate optical labels. Systems designed for array-based detection are particularly useful.

For example, optical systems for use with the methods set forth herein may be constructed to include various components and assemblies as described in U.S. Pat. Nos. 8,241,573; 7,329,860 and 8,039,817; and US Pat. App. Pub. Nos. 2009/0272914 A1 and 2012/0270305 A1, each of which is incorporated herein by reference.

As set forth above, a method of the present disclosure can include two orthogonal primer extension steps. For example, a method is set forth above that includes inter alia the steps of (b) extending a first primer bound to a first nucleic acid using a first polymerase species and a first set of nucleotide analogs, thereby producing a first primer extension product having a first nucleotide analog at each of the sites; and (c) extending a second primer bound to a second nucleic acid using a second polymerase species and a second set of nucleotide analogs, thereby producing a second primer extension product having a second nucleotide analog at each of the sites, wherein the first polymerase species is different from the second polymerase species and wherein the first set of nucleotide analogs is different from the second set of nucleotide analogs. In some embodiments steps (b) and (c) are carried out simultaneously. Alternatively, steps (b) and (c) can be carried out sequentially, in any order. In either case, the orthogonality of the primer extension reactions allows the two extension products to be distinguished. Thus, both extension products can be simultaneously present during a detection step and need not be spatially resolved by the detector used.

A multiplex reaction can utilize a solid-phase support. A solid-phase support can be useful for separating individual reactions such that each can be interrogated separately or individually. For example, several different nucleic acids in a mixture can be attached to the solid-phase support. The nucleic acids can be attached to the solid-phase support in an array format.

In some embodiments, an array of sites is provided, wherein each site includes a first nucleic acid template and a second nucleic acid template and wherein the first nucleic acid template has a sequence that is different from the sequence of the second nucleic acid template. Exemplary arrays that can be useful include, without limitation, a BeadChip Array available from Illumina®, Inc. (San Diego, Calif.) or arrays such as those described in U.S. Pat. Nos. 6,266,459; 6,355,431; 6,770,441; 6,859,570; or U.S. Pat. No. 7,622,294; or PCT Publication No. WO 00/63437, each of which is incorporated herein by reference. Further examples of commercially available arrays that can be used include, for example, an Affymetrix® GeneChip® array or other array synthesized in accordance with techniques sometimes referred to as VLSIPS™ (Very Large Scale Immobilized Polymer Synthesis) technologies. A spotted array can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies.

Other useful arrays include those that are used in nucleic acid sequencing applications. For example, arrays having amplicons of genomic fragments (often referred to as clusters) are particularly useful such as those described in Bentley et al., Nature 456:53-59 (2008), WO 04/018497; U.S. Pat. No. 7,057,026; WO 91/06678; WO 07/123744; U.S. Pat. No. 7,329,492; U.S. Pat. No. 7,211,414; U.S. Pat. No. 7,315,019; U.S. Pat. No. 7,405,281, or US 2008/0108082, each of which is incorporated herein by reference. Nucleic acid clusters can be created by solid-phase amplification methods. For example, a nucleic acid having one or more template sequences to be detected can be attached to a surface and amplified using bridge amplification. Useful bridge amplification methods are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference. Another useful method for amplifying nucleic acids on a surface is rolling circle amplification (RCA), for example, as described in Lizardi et al., Nat. Genet. 19:225-232 (1998) and US Pat. App. Pub. No. 2007/0099208 A1, each of which is incorporated herein by reference. Another type of array that is useful is an array of particles produced from an emulsion PCR amplification technique. Examples are described in Dressman et al., Proc. Natl. Acad. Sci. USA 100:8817-8822 (2003), WO 05/010145, US 2005/0130173 or US 2005/0064460, each of which is incorporated herein by reference. Although the above arrays have been described in the context of sequencing applications, it will be understood that the arrays can be used in other embodiments including, for example, those that use a non-cyclic primer extension technique.

Detection can be carried out at ensemble or single molecule levels on an array. Ensemble level detection is detection that occurs in a way that several copies of a single template sequence are detected at each individual site and individual copies at the site are not distinguished from each other. Thus, ensemble detection provides an average signal from a particular template sequence at the site. For example, the site can contain at least 10, 100, 1000 or more copies of a particular template sequence. Of course, a site can contain multiple different template sequences each of which is present as an ensemble. Alternatively, detection at a single molecule level includes detection that occurs in a way that individual template sequences are individually resolved on the array, each at a different site. Thus, single molecule detection provides a signal from an individual molecule that is distinguished from one or more signals that may arise from a population of molecules within which the individual molecule is present. Of course, even in a single molecule array, a site can contain several different template sequences (e.g. two or more template sequence regions located along a single nucleic acid molecule).

An array of sites can appear as a grid of spots or patches. The sites can be located in a repeating pattern or in an irregular non-repeating pattern. Particularly useful patterns are hexagonal patterns, rectilinear patterns, grid patterns, patterns having reflective symmetry, patterns having rotational symmetry, or the like. Asymmetric patterns can also be useful.

The size of the sites and/or spacing between the sites in an array can vary to achieve high density, medium density or lower density. High density arrays are characterized as having sites separated by less than about 15 µm. Medium density arrays have sites separated by about 15 to 30 µm, while low density arrays have sites separated by greater than 30 µm. An array useful in some embodiments can have sites that are separated by less than 100 µm, 50 µm, 10 µm, 5 µm, 1 µm, or 0.5 µm. An embodiment of the methods set forth herein can be used to image an array at a resolution sufficient to distinguish sites at the above densities or density ranges. However, the detecting step will typically use a detector having a spatial resolution that is too low to resolve points at distance equivalent to the spacing between the first primer extension product and the second primer extension product at each of the sites. In particular embodiments, sites of an array can each have an area that is larger than about 100 nm2, 250 nm2, 500 nm2, 1 µm2, 2.5 µm2, 5 µm2, 10 µm2, 100 µm2, or 500 µm2. Alternatively or additionally, sites of an array can each have an area that is smaller than about 1 mm2, 500 µm2, 100 µm2, 25 µm2, 10 µm2, 5 µm2, 1 µm2, 500 nm2, or 100 nm2. Indeed, a site can have a size that is in a range between an upper and lower limit selected from those exemplified above.

The methods set forth herein can use arrays having sites at any of a variety of densities including, for example, at least about 10 sites/cm2, 100 sites/cm2, 500 sites/cm2, 1,000 sites/cm2, 5,000 sites/cm2, 10,000 sites/cm2, 50,000 sites/cm2, 100,000 sites/cm2, 1,000,000 sites/cm2, 5,000,000 sites/cm2, or higher.

An orthogonal detection system, such as a system used for sequencing-by-orthogonal-synthesis, can use different labels to distinguish different nucleotides that are added to each primer. In one embodiment, each nucleotide species will have a unique optical label that produces a unique signal for distinguishing that nucleotide species. An example is the 4-dye SBOS approach described in Example I, below, and shown in FIG. 1A and FIG. 1B. In this example, a first set of 4 different fluorescent dyes is used to distinguish the 4 different dNTP analogs from each other and a second set of 4 different fluorescent dyes is used to distinguish the 4 different rNTP analogs from each other. The two sets of dyes are unique such that the 8 dyes produce 8 distinguishable signals, respectively.

In embodiments where all of the nucleotides are distinguishably labeled, such as the 4-dye SBOS approach, a pair of template sequences can be contacted with all of the nucleotides and then detection can be performed afterwards. Here the ability to distinguish all of the nucleotides due to unique optical labels provides the benefit of relatively simple fluidic manipulations, whereby all of the nucleotides can be delivered to the template sequences such that they are simultaneously present. In a relatively straightforward and preferred SBOS embodiment all 8 nucleotides are delivered simultaneously; however, one or more subsets can be delivered sequentially if desired. Detection can occur during or after nucleotide delivery. This relatively simple fluidic process is accommodated by a relatively complex detection device having the ability to distinguish all of the signals. For example, a fluorescence detection system able to distinguish 8 different fluorescent signals can be used for an SBOS approach that utilizes 8 different fluorescently labeled nucleotides. Those skilled in the art will know or be able to determine an appropriate fluorescent detection apparatus to achieve this sort of signal differentiation. For example, excitation and emission properties of the fluorescent labels can be appropriately matched with a combination of excitation wavelengths produced and emission wavelengths detected by a fluorometer. Exemplary guides for optics and labels useful for multiwavelength fluorescence detection are provided in Lakowicz, Principles of Fluorescence Spectroscopy, 3rd Ed. Springer (2006); Haugland, Handbook of Fluorescent Probes and Research Products 9th Ed., Molecular Probes, Inc, (2002); and Shapiro, Practical Flow Cytometry, 4th Ed., John Wiley & Sons (2003), each of which is incorporated herein by reference.

The principles exemplified above for a system in which all of the nucleotides are distinguishably labeled, can be readily extended to an array format. An array having a sufficient number and variety of different template sequences will be expected to incorporate all of the labeled nucleotides when treated with primer extension reaction systems. More specifically, in an array-based SBOS approach, having a wide variety of nucleic acids across the array sites and having two different templates per site, all possible 2-dye dye combinations will be expected to occur on the array following a primer extension cycle in which all 8 nucleotides were delivered to the array. The sites can be spatially distinguished using optical devices known in the art, for example, those described in U.S. Pat. Nos. 8,241,573; 7,329,860 and 8,039,817; and US Pat. App. Pub. Nos. 2009/0272914 A1 and 2012/0270305 A1, each of which is incorporated herein by reference. Such detection systems can be readily modified to accommodate 8-color fluorescent detection as set forth above. A detection system that is modified in this way will be capable of multiplex orthogonal detection such that two different templates are distinguished (e.g. via sequencing) at multiple sites each having a different sequence composition.

In some embodiments, the number of different signals that are distinguished in a particular method is less than the number of different nucleotide species used in that method. For example, multiple different nucleotide species can have the same label and/or a subset of the nucleotide species can be unlabeled. An example of a configuration that uses the same label for multiple different nucleotide species is the case of an orthogonal primer extension (or SBOS) method where 4 different deoxyribonucleotides have a first label in common and 4 different ribonucleotides have a second label in common. In this configuration, the 4 different deoxyribonucleotides can be distinguished from each other by sequential cycles of delivering one of the deoxyribonucleotides and detecting the deoxyribonucleotides prior to delivering the subsequent deoxyribonucleotide. So long as the first label and second label in this example are distinguishable, the deoxyribonucleotides and ribonucleotides can be delivered in pairs (1 each of a single deoxyribonucleotide species and a single ribonucleotide species), in 4 cycles of delivery and detection. Thus, members of a first set of nucleotide analogs used in a primer extension reaction (e.g. dNTPs) can include only one type of optical label that gets detected and a second set of nucleotide analogs, that is orthogonal to the first set (e.g. rNTPs) can also include only one type of optical label that gets detected, wherein the label used in the first set is optically distinguishable from the label used in the second set.

Greyscaling allows use of multiple different nucleotide species that have the same label. Here different nucleotide species can be distinguished based on the intensity of label signal detected. For example, each species of nucleotide can be delivered as a uniquely proportioned mixture of that species of nucleotide in labeled and unlabeled form. Variation in the ratio of labeled: unlabeled nucleotide for each species will result in a uniquely greyscaled signal output for each mixture. By way of more specific example, a first nucleotide can be fully labeled (no mixing of labeled and unlabeled first nucleotide), a second nucleotide can be 75% labeled (a mix of 75% labeled second nucleotide and 25% unlabeled second nucleotide), a third nucleotide can be 50% labeled (a mix of 50% labeled third nucleotide and 50% unlabeled third nucleotide), and a fourth nucleotide can be 25% labeled (a mix of 25% labeled fourth nucleotide and 75% unlabeled fourth nucleotide). These 4 nucleotide species can be distinguished based on the resulting differences in signal intensity, whereby a population of primers (e.g. at an array site) will produce full signal due to incorporation of the first nucleotide; 75% signal due to incorporation of the second nucleotide, 50% signal due to incorporation of the third nucleotide and 25% signal due to incorporation of the fourth nucleotide.

In particular embodiments, at least one of the nucleotide species can be entirely unlabeled. Thus, in a case where optical labels are present on the other nucleotides in a set of nucleotide, there can also be a 'dark' nucleotide. Extension of a primer to incorporate a dark, or otherwise unlabeled, nucleotide can be determined by inference based on the absence of a label that would be expected if the other nucleotides in the set were to have been incorporated by the extension reaction. Thus, in some embodiments only a subset of the nucleotides used in a primer extension reaction set forth herein need to have a label.

Use of entirely unlabeled nucleotide species can be combined with greyscaling. For example, three of four different nucleotide species in a set can have distinguishable nonzero amounts of a particular label (e.g. ratios of labeled and non-labeled nucleotides in a mixture) and the fourth nucleotide species can lack that label. Alternatively or additionally, greyscaling can be combined with use of several optically distinguishable labels. For example, some nucleotide species can be represented in an extension reaction as a mixture of nucleotides of the same type but having different labels. Such a configuration is exemplified in Example I below where a nucleotide species is provided as a mixture of 50% rtrCTP-Fred/50% rtrCTP-Fblue. Further examples of greyscaling and mixed labels that can be modified for use in an orthogonal method of the present disclosure are set forth in US 2013/0079232 A1, which is incorporated herein by reference.

Alternatively or additionally to the use of multiple different labels, greyscaling, and/or unlabeled species, an embodiment set forth herein can use a nucleotide having a ligand, cleavable linker or other moiety that provides for gain or loss of a label due to a defined treatment. Reagent systems of this type are illustrated in Example I below where some nucleotide species have a ligand such that they can be distinguished from other nucleotides based on initial absence of a detectable signal followed by appearance of a signal after treatment with an appropriately labeled receptor. Example I also illustrates use of a nucleotide that can be distinguished based on an initial detectable signal that is subsequently lost or at least reduced due to treatment with a reagent that modifies the label (e.g. via chemical cleavage of a linker between the label and nucleotide). In this case the other nucleotide species in the set are not susceptible to the modification (e.g. lacking the cleavable linker) and are distinguished based on persistence of signal generation after the treatment.

As exemplified above and in Example I, in some embodiments, a label can be attached to a nucleotide analog via a cleavable linker. In particular embodiments, photocleavable linkers can be used in place of the chemically cleavable linker exemplified above. In some embodiments, the linker is selected from acid labile linkers (including dialkoxybenzyl linkers, Sieber linkers, indole linkers, t-butyl Sieber linkers), electrophilically cleavable linkers, nucleophilically cleavable linkers, photocleavable linkers, linkers that are cleaved under reductive conditions or oxidative conditions, safety-catch linkers, and linkers that are cleaved by elimination mechanisms. In some such embodiments, the linker is selected from a disulfide linker (—S—S—), ester, nitrobenzene, imine, enzymatically or chemically cleavable peptide and polynucleotide, such as DNA.

In some embodiments, members of a first set of nucleotide analogs used in a primer extension reaction (e.g. dNTPs) will include only one type of optical label that gets detected and a second set of nucleotide analogs, that is orthogonal to the first set (e.g. rNTPs) will also include only one type of optical label that gets detected, wherein the label used in the first set is optically distinguishable from the label used in the second set. In this embodiment, the one type of optical label can be attached to substantially all of the nucleotide analogs of a first species in the first set, the one type of optical label can be attached to a subset of the nucleotide analogs of a second species in the first set, substantially all of the nucleotide analogs of a third species in the first set can be attached to a ligand, and substantially all of the nucleotide analogs of a fourth species in the first set are not attached to the one type of optical label or to the ligand.

In another embodiment, members of a first set of nucleotide analogs used in a primer extension reaction (e.g. dNTPs) will include only two types of optical labels that get detected and a second set of nucleotide analogs, that is orthogonal to the first set (e.g. rNTPs) will also include only two types of optical label that get detected. In this embodiment, a first of the two types of optical labels can be attached to substantially all of the nucleotide analogs of a first species in the first set, a second of the two types of optical labels can be attached to substantially all of the nucleotide analogs of a second species in the first set, the first of the two types of optical labels and the second of the two types of optical labels can be attached to nucleotide analogs of a third species in the first set, and substantially all of the nucleotide analogs of a fourth species in the first set are not attached to the one of the two types of optical labels or the second of the two types of optical labels.

It will be understood from the above examples, that reducing the number of different labels in an orthogonal detection system can provide the advantage of reducing the complexity of the detection device needed to distinguish addition of different nucleotides to a template-bound primer. However, in many embodiments this is achieved by increasing the complexity of the fluidic steps such that the number of fluidic manipulations used during detection steps is increased compared to the fluidic steps used when each of the nucleotide species has a unique label. A general advantage of the present methods is that one skilled in the art can select an appropriate combination of labels, fluidic steps and detection devices to suit a particular application or circumstance.

The present disclosure provides reaction mixtures (also referred to herein as reagent systems) that include various combinations of components. In several cases reaction components and several combinations of the components are described in the context of exemplary methods. It will be understood that the reaction mixtures and the components thereof need not be limited to use in the methods exemplified herein. Other uses are contemplated as well. Accordingly, the components can be assembled, in a variety of useful combinations, for example to create kits. The kits can be useful for storage, transportation or commercial transaction of the components set forth herein. The kits can optionally include instructions for carrying out one or more of the methods set forth herein.

The following examples are intended to illustrate but not limit the present invention.

Example I

Two-Primer Sequencing-by-Orthogonal-Synthesis

This Example describes a new sequencing platform that allows for doubling the sequencing output when compared to traditional sequencing-by-synthesis (SBS).

Figure 1B:
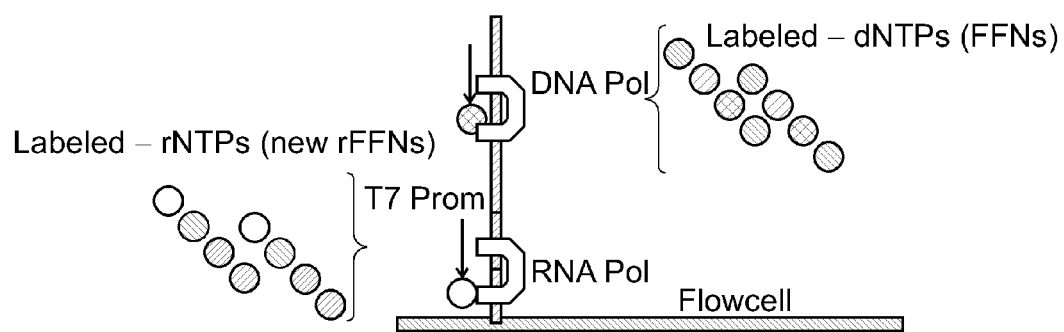

This platform capitalizes on SBS in that sequencing information derives from a step-wise elongation of the sequencing primer (FIG. 1A) However, in the new platform, the elongation event at the first site occurs in parallel to a second sequencing elongation event, occurring at a second site downstream from the first site (FIG. 1B).

Orthogonality between SBS sites 1 and 2 is provided by the use of two different polymerases and substrate combinations. As exemplified below, the system can use an SBS DNA polymerase and fully functional nucleotides (FFNs), such as those available from Illumina, Inc. (San Diego, Calif.), in combination with an RNA polymerase (e.g. T7 RNA pol.) and corresponding labeled rNTPs (FIG. 1C). Although discrimination in substrate specificity between RNA and DNA polymerases is not absolute, the difference in substrate preference between rNTPs and dNTPs has been shown to be as high as 10000-fold in certain conditions (Joyce, Proc. Nat'l. Acad. Sci. USA, 94:1619-1622 (1997) and Gao et al, Proc. Nat'l. Acad. Sci. USA, 94:407-411 (1997), each of which is incorporated herein by reference). Alternatively, an orthogonal system can be achieved by exploiting synthetic DNA/RNA analogues (XNAs) and a corresponding engineered polymerase. Such a system is possible using DNA-templated synthesis of long HNAs (1,5 anhydrohexitol nucleic acids) with an evolved DNA polymerase. Exemplary conditions and reagents that can be used for DNA-templated synthesis of long HNAs are described in Pinheiro et al, Science, 336 (6079):341-344 (2012) and Cozens et al, Proc. Nat'l. Acad. Sci. USA, 109 (21):8067-8072 (2012), each of which is incorporated herein by reference.

Signal Discrimination

The following exemplary configurations can be used for signal discrimination in a sequencing-by-orthogonal-synthesis (SBOS) platform.

(1) 4-Dye SBOS Chemistry Based Approach.

In this approach, a set of four reversible terminator deoxyribonucleotides (rtdNTPS) is used in which each of the rtdNTP species has a fluorophore that is optically distinguishable from the fluorophores used for the other three rtdNTP species. This is akin to the combination of nucleotides used in commercially available 4-dye SBS platforms available from Illumina, Inc. (San Diego, Calif.). A set of four reversible terminator ribonucleotides (rtrNTPs) is also used and each of the rtrNTP species has a fluorophore that is optically distinguishable from the fluorophores used for the other three rtrNTP species. Furthermore, the fluorophores used for the rtdNTPS are optically distinguishable from the fluorophores for the rtrNTPS. As such there are 8 different fluorophores in use across the two sets of nucleotides. Table 1 shows an exemplary set where the subscript refers to the emission wavelength for each fluorophore (F).

TABLE 1

Nucleotides for 4-dye SBS configuration

| rtdNTP set | rtrNTP set |
|---|---|
| rtdTTP-$F_{far-red}$ | rtrUTP-$F_{green}$ |
| rtdCTP-$F_{near-red}$ | rtrCTP-$F_{blue}$ |
| rtdGTP-$F_{orange}$ | rtrGTP-$F_{indigo}$ |
| rtdATP-$F_{yellow}$ | rtrATP-$F_{violet}$ |

In the 4-dye approach, the optical components used to distinguish the 8 different fluorophores may be relatively complex, for example, using up to eight different emission channels and/or up to eight different excitation lines.

(2) 1-Dye SBOS Chemistry Based Approach.

In order to reduce the complexity of the optical device described for the 4-dye approach, another approach that uses fewer fluorophores than nucleotide species can be used. A 1-dye approach can use a set of rtdNTPs having a single fluorophore of a first type (e.g. a blue emitting fluorophore). The different species of rtdNTPs can be distinguished from each other due to the presence of the fluorophore on a first species in the set of rtdNTPs (e.g. rtdTTP-blue emitting fluorophore), the presence of a binding ligand on a second species in the set of rtdNTPs (e.g. rtdCTP-Biotin), the absence of the fluorophore and binding ligand on a third species in the set of rtdNTPs (e.g. unlabeled rtdGTP) and the attachment the fluorophore via a cleavable linker to a fourth species in the set of rtdNTPs (e.g. rtdATP-disulfide linkage-blue emitting fluorophore). Exemplary combinations of fluorophore-labeled, ligand-labeled, and unlabeled nucleotide species that can be used to create a set of nucleotides for 1-dye detection are set forth in further detail in US 2013/0079232 A1, which is incorporated herein by reference.

The 1-dye approach can further use a set of rtrNTPS having a second type of fluorophore. The second type of fluorophore (e.g. a red emitting fluorophore) is optically distinguishable from the fluorophore used for members of the of rtdNTP set. Moreover, the individual species in the set of rtrNTPs can be distinguished from each other by a combination of labeled and unlabeled species similar to the combination exemplified above for the rtdNTP set, with the following modification. In order to avoid the introduction of a new Biotin-Steptavidin system, one of the rtrNTPs can be a mix of the two fluorophores in use. An exemplary set of nucleotides is shown in Table 2 (a similar set is shown in FIG. 2A).

TABLE 2

Nucleotides for 1-dye SBS configuration

| rtdNTP set | rtrNTP set |
|---|---|
| rtdTTP-$F_{blue}$ | rtrUTP-$F_{red}$ |
| rtdCTP-Biotin | 50% rtrCTP-$F_{red}$/50% rtrCTP-$F_{blue}$ |
| rtdGTP (unlabeled) | rtrGTP (unlabeled) |
| rtdATP-S-S-$F_{blue}$ | rtrATP-S-S-$F_{red}$ |

For an SBOS approach using the configuration of Table 2, the optical components need only include 2 different emission channels and only 1 or 2 different excitation lines. In this approach, as shown in FIG. 2A, a total of 4 images are acquired per cycle (2 per color). Two images are recorded before and two after treatment with streptavidin-$F_{blue}$. In FIG. 2A and FIG. 2B, "dark" indicates the absence of fluorophore label, "NR550C4" is the blue-emitting fluorophore, "THP" is Tris(3-hydroxypropyl)phosphine which cleaves disulfide linkage ("SS"), "Strep" is streptavidin, "d-FFN" is rtdNTP, "r-FFN" is rtrNTP and "red" is the red emitting fluorophore.

Although the mixture of rtrCTP-labeled species is exemplified above as a 1:1 molar ratio (i.e. 50% $F_{red}$ and 50% $F_{blue}$), it will be understood that other ratios can be used instead. For example, it may be desirable to adjust the ratio to accommodate different optical properties for the two fluorophores (e.g. one of the fluorophores can be present at a slight molar excess to accommodate a relatively lower emission intensity than the other fluorophore at the detection wavelength being used). The ratio can also deviate from 1:1 to accommodate different biochemical properties of the labeled nucleotides (e.g. different affinity for polymerase).

(3) 2-Dye SBOS Chemistry Based.

This approach provides another combination of nucleotides with fewer fluorophores than nucleotide species. A set of rtrNTPs can be used having fluorophores with two different emissions (e.g. far-red and blue emission). Similarly, a set of rtdNTPs can be used having fluorophores with two different emissions. The four different emissions are optically distinguishable across the two sets of rtNTPs. An exemplary set of nucleotides is shown in Table 3.

TABLE 3

Nucleotides for 2-dye SBS configuration

| rtdNTP set | rtrNTP set |
|---|---|
| 50% rtdTTP-$F_{green}$/50% rtdTTP-$F_{red}$ | rtrUTP-$F_{far\text{-}red}$ |
| rtdCTP-$F_{red}$ | 50% rtrCTP-$F_{far\text{-}red}$/50% rtrCTP-$F_{blue}$ |
| rtdGTP (unlabeled) | rtrGTP (unlabeled) |
| rtdATP-$F_{green}$ | rtrATP-$F_{blue}$ |

The 2-dye approach exemplified above, provides an advantage over the previously exemplified 1-dye approach in that chemical processing steps, such as streptavidin binding and THP cleavage, are not used during the detection phase of the 2-dye approach. This is demonstrated by the extension cycle protocol shown for the 2-dye approach in FIG. 3. However, in the case of this particular 2-dye approach, an optical device capable of distinguishing four different colors is used. As illustrated by this comparison, different approaches can be used to adjust optical complexity or fluidic complexity to suit a particular sequencing platform. For example, by adding fluidic steps to modify nucleotides during an SBS detection cycle one can use fewer and/or simpler optical components. Conversely, in cases where more complex optical components are available, fewer and/or simpler fluidic manipulations can be used.

Sample Preparation

A genomic DNA or other nucleic acid sample can be prepared for 2-Primer SBS as exemplified in FIG. 4. The method allows creation of a DNA template having two different priming sites. The method can be carried out under conditions that provide fragments in a desired size range. As shown in FIG. 4, a transposase can be used to tagment a genomic DNA sample with two different tag sequences. Conditions can be selected to produce fragments that are on average about 300 nucleotides long and that have a first tag at one end and a second tag at the other end. The tags will form single stranded overhangs to which adapters can hybridize. Ligation of the hybridized adapters as shown in FIG. 4 will yield 2-fragment concatamers having the following order of sequence regions: a p5 sequence, Read 1 priming site, DNA fragment 1, RNA polymerase promoter, Read 1' priming site, DNA fragment 2, index and p7 sequence. The p5 and p7 sequences at the end of the concatamers allow capture and bridge amplification, for example, using sequencing flow cells and kits available from Illumina, Inc. (San Diego, Calif.). The Read 1 priming sites is complementary to a DNA primer to be extended by DNA polymerase and the Read 1' priming site is complementary to an RNA primer to be extended by RNA polymerase, respectively, in the orthogonal SBS reaction. The RNA polymerase promoter is downstream of the RNA polymerase priming site to activate RNA polymerase activity. DNA fragment 1 is downstream of the DNA polymerase priming site and as such is positioned for detection by DNA polymerase extension in the SBS reaction and DNA fragment 2 is downstream of the RNA polymerase priming site and as such is positioned for detection by RNA polymerase extension in the SBS reaction. The index is optionally available for sample tracking purposes.

Overall, the platform provided by this example is expected to increase sequencing output by doubling the sequencing information per cycle; i.e. a 2-Primer SBS 150 cycle run would be equivalent to a commercially available SBS paired end 2×150 cycle run (Illumina, Inc., San Diego Calif.), but with additional savings in run time and reagent usage. If implemented in paired end format, a 2-Primer SBS paired end 2×75 cycle run would be equivalent to a traditional 2×150 paired end run.

Throughout this application various publications, patents and patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

What is claimed is:

1. A method for sequencing nucleic acid templates, comprising
    (a) providing an array of sites, wherein each site comprises a first nucleic acid template and a second nucleic acid template,
    wherein the first nucleic acid template has a sequence that is different from the sequence of the second nucleic acid template;
    (b) extending a DNA primer bound to the first template using a DNA ligase species and a set of probe oligonucleotides, thereby producing a DNA primer extension product comprising a probe oligonucleotide at each of the sites;
    (c) extending an RNA primer bound to the second template using an RNA polymerase species and a set of ribonucleotide analogs, thereby producing an RNA primer extension product comprising a ribonucleotide analog at each of the sites;
    (d) detecting the DNA primer extension product and the RNA primer extension product at each of the sites; and
    (e) repeating steps (b) through (d), thereby determining the different sequences of the first template and the second template at each of the sites.

2. The method of claim 1, wherein the detecting uses a detector having a spatial resolution that is too low to resolve points at distance equivalent to the spacing between the DNA primer extension product and the RNA primer extension product at each of the sites.

3. The method of claim 2, wherein the detector is an optical detector.

4. The method of claim 3, wherein the probe oligonucleotides comprise optical labels.

5. The method of claim 3, wherein the ribonucleotide analogs comprise optical labels.

6. The method of claim 5, wherein the optical labels of the probe oligonucleotides are different from the optical labels of the ribonucleotide analogs.

7. The method of claim 2, wherein a pixel of the detector acquires signals from both the DNA primer extension product and the RNA primer extension product.

8. The method of claim 1, wherein the first nucleic acid template and the second nucleic acid template comprise DNA.

9. The method of claim 1, wherein steps (b) and (c) are carried out simultaneously.

10. The method of claim 1, wherein steps (b) and (c) are carried out sequentially.

11. The method of claim 1, wherein a single nucleic acid molecule contains the first nucleic acid template and the second nucleic acid template.

12. The method of claim 1, wherein the first nucleic acid template and the second nucleic acid template are on different nucleic acid molecules.

13. The method of claim 1, wherein the sites have an area that is no greater than 100 µm².

14. The method of claim 1, wherein the sites comprise multiple copies of the first nucleic acid template and the second nucleic acid template.

15. The method of claim 1, wherein the DNA ligase is selective for the first template compared to the second template and wherein the RNA polymerase is selective for the second template compared to the first template.

16. A method for sequencing nucleic acid templates, comprising
 (a) providing a first nucleic acid template and a second nucleic acid template,
 wherein the first nucleic acid template has a sequence that is different from the sequence of the second nucleic acid template;
 (b) extending a DNA primer bound to the first template using a DNA ligase species and a set of probe oligonucleotides, thereby producing a DNA primer extension product comprising a probe oligonucleotide;
 (c) extending an RNA primer bound to the second template using an RNA polymerase species and a set of ribonucleotide analogs, thereby producing an RNA primer extension product comprising a ribonucleotide analog,
 (d) detecting the DNA primer extension product and the RNA primer extension product using a detector having a resolution that is lower than the spatial separation between the DNA primer extension product and the RNA primer extension product; and
 (e) repeating steps (b) through (d), thereby determining the different sequences of the first template and the second template.

17. The method of claim 16, wherein the detector is an optical detector, and wherein the probe oligonucleotides comprise optical labels.

18. The method of claim 17, wherein the ribonucleotide analogs comprise optical labels.

19. The method of claim 18, wherein the optical labels of the probe oligonucleotides are different from the optical labels of the ribonucleotide analogs.

20. The method of claim 16, wherein steps (b) and (c) are carried out simultaneously.

21. The method of claim 16, wherein steps (b) and (c) are carried out sequentially.

22. The method of claim 16, wherein a single nucleic acid molecule contains the first nucleic acid template and the second nucleic acid template.

23. The method of claim 16, wherein the first nucleic acid template and the second nucleic acid template are on different nucleic acid molecules.

24. The method of claim 16, wherein the sites comprise multiple copies of the first nucleic acid template and the second nucleic acid template.

* * * * *